US00PP36153P2

(12) United States Plant Patent
van Dijk

(10) Patent No.: US PP36,153 P2
(45) Date of Patent: Sep. 24, 2024

(54) ***ANTHURIUM* PLANT NAMED 'AN2143048'**

(50) Latin Name: *Anthurium andreanum*
Varietal Denomination: AN2143048

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/537,558

(22) Filed: Dec. 12, 2023

(51) Int. Cl.
*A01H 5/02* (2018.01)
*A01H 6/10* (2018.01)

(52) U.S. Cl.
USPC ..... Plt./369

(58) Field of Classification Search
USPC ..... Plt./369
CPC ..... A01H 5/02; A01H 5/00; A01H 6/10
See application file for complete search history.

(56) References Cited

U.S. PATENT DOCUMENTS

PP33,711 P2 * 11/2021 Van Dijk ..... Plt./365

OTHER PUBLICATIONS

CPVO Register version 4.17.26 for *Anthurium* AN2143048 retrieved on Apr. 22, 2024 at https://online.plantvarieties.eu/publicConsultation Details?registerId=20222624&denomination=an2143048, 2 pp. (Year: 2024).*

Upov Pluto 20240419 retrieved on Apr. 22, 2024 at https://pluto.upov.int/result, one page. (Year: 2024).*

* cited by examiner

*Primary Examiner* — June Hwu

(74) *Attorney, Agent, or Firm* — C. Anne Whealy

(57) ABSTRACT

A new and distinct cultivar of Anthurium plant named 'AN2143048', characterized by its upright to outwardly arching and uniform plant habit; freely clumping growth habit; bushy and dense plants; glossy dark green-colored leaves; freely flowering habit; inflorescences that are positioned within to slightly above the foliar plane on strong and erect scapes; broad, concave, glossy and vivid red-colored spathes and purplish red-colored spadices; and good inflorescence longevity.

2 Drawing Sheets

Figure 1:
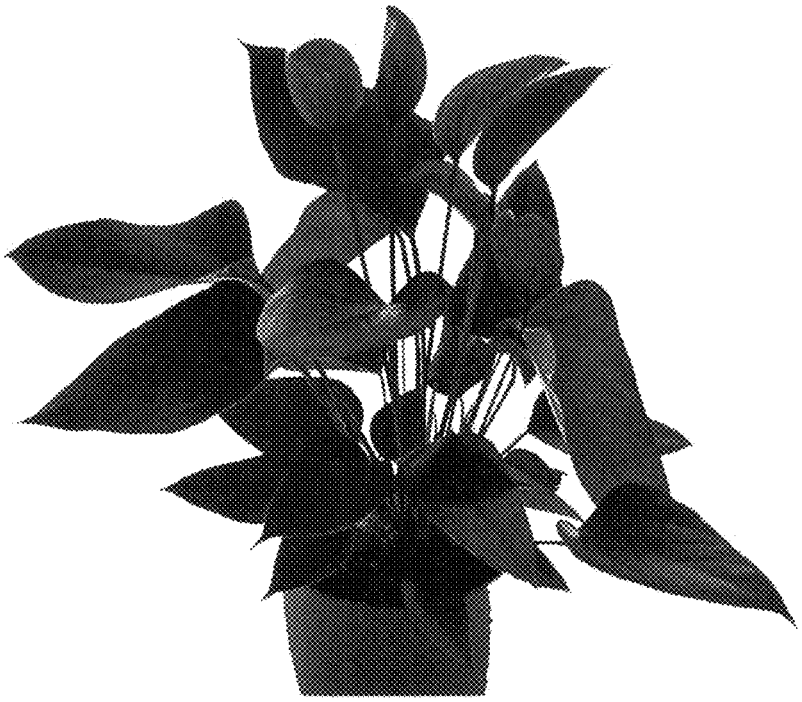

Botanical designation: *Anthurium andreanum.*
Cultivar denomination: 'AN2143048'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Anthura B.V. of Bleiswijk, The Netherlands on Nov. 22, 2022, application number 2022/2624. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of Anthurium plant, botanically known as *Anthurium andreanum* and hereinafter referred to by the name 'AN2143048'.

The new Anthurium plant is a product of a controlled breeding program conducted by the Inventor in Bleiswijk, The Netherlands. The objective of the breeding program is to create new vigorous Anthurium plants with durable, broad and glossy red-colored spathes.

The new Anthurium plant originated from a cross-pollination made by the Inventor in September, 2013 in Bleiswijk, The Netherlands of a proprietary selection of *Anthurium andreanum* identified as code number 10-024898-001, not patented, as the female, or seed, parent with a proprietary selection of *Anthurium andreanum* identified as code number 11-026817-0018, not patented, as the male, or pollen, parent. The new Anthurium was discovered and selected by the Inventor as a single flowering plant within the progeny of the stated cross-pollination in a controlled greenhouse environment in Bleiswijk, The Netherlands in August, 2015.

Asexual reproduction of the new Anthurium plant by in vitro meristem propagation in a controlled environment in Bleiswijk, The Netherlands since September, 2017 has shown that the unique features of this new Anthurium are stable and reproduced true to type in successive generations of asexual reproduction.

SUMMARY OF THE INVENTION

Plants of the new Anthurium have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2143048'. These characteristics in combination distinguish 'AN2143048' as a new and distinct Anthurium plant:

1. Upright to outwardly arching and uniform plant habit.
2. Freely clumping growth habit; bushy and dense plants.
3. Glossy dark green-colored leaves.
4. Freely flowering habit.
5. Inflorescences that are positioned within to slightly above the foliar plane on strong and erect scapes.
6. Broad, concave, glossy and vivid red-colored spathes and purplish red-colored spadices.
7. Durable spathes impart good inflorescence longevity.

Plants of the new Anthurium differ from plants of the female parent selection in the following characteristics:

1. Spathes of plants of the new Anthurium are broader than spathes of plants of the female parent selection.
2. Peduncles of plants of the new Anthurium are slightly tinged with anthocyanin whereas peduncles of plants of the female parent selection are strongly tinged with anthocyanin.

Plants of the new Anthurium differ from plants of the male parent selection in the following characteristics:

1. Spathes of plants of the new Anthurium are vivid red in color whereas spathes of plants of the male parent selection are orange in color.
2. Spadices of plants of the new Anthurium are purplish red in color whereas spadices of plants of the male parent selection are white to creamy white in color.

Plants of the new Anthurium can also be compared to plants of *Anthurium andreanum* 'Anthfuncni', disclosed in U.S. Plant Pat. No. 33,711. In side-by-side comparisons, plants of the new Anthurium differ from plants of 'Anthfuncni' in the following characteristics:

1. Inflorescences of plants of the new Anthurium have longer spadices than inflorescences of plants of 'Anthfuncni'.
2. Spadices of plants of the new Anthurium are purplish red in color whereas spadices of plants of 'Anthfuncni' are white in color with yellowish green-colored apices.

BRIEF DESCRIPTION OF THE PHOTOGRAPHS

The accompanying photographs illustrate the overall appearance of the new Anthurium. The photographs show the colors as true as it is reasonably possible to obtain in colored reproductions of this type. Colors in the photographs may differ slightly from the color values cited in the detailed botanical description which accurately describe the colors of the new Anthurium.

The photograph on the first sheet (FIG. 1) is a side perspective view of a typical plant of 'AN2143048' grown in a container.

Figure 2:
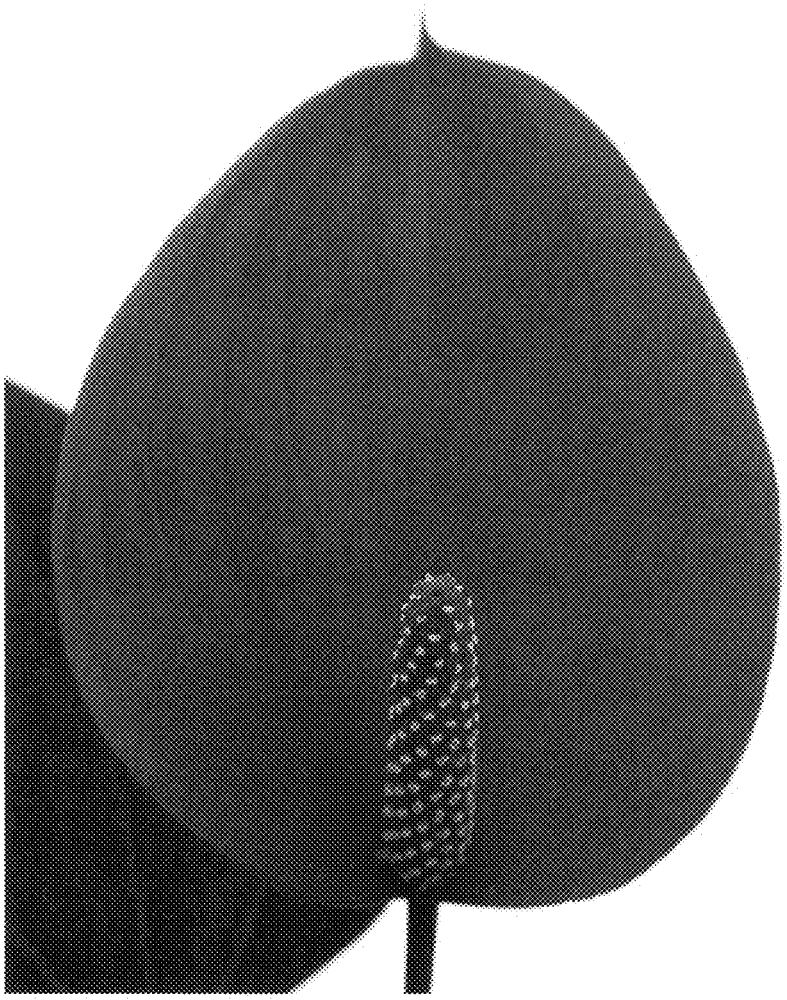

The photograph on the second sheet (FIG. 2) is a close-up view of a typical inflorescence of 'AN2143048'.

DETAILED BOTANICAL DESCRIPTION

The aforementioned photographs and following observations and measurements describe plants grown in 17-cm containers in Bleiswijk, The Netherlands during the summer in a glass-covered greenhouse. Plants were grown under conditions and practices which approximate those generally used in commercial Anthurium production. During the production of the plants, day and night temperatures ranged from about 19 C. to 22.5 C. Plants were one year old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2143048'.

Parentage:

*Female, or seed, parent.*—Proprietary selection of *Anthurium andreanum* identified as code number 10-024898-0001, not patented.

*Male, or pollen, parent.*—Proprietary selection of *Anthurium andreanum* identified as code number 11-026817-0018, not patented.

Propagation:

*Type.*—By in vitro meristem propagation.

*Time to initiate roots, summer and winter.*—About two weeks at temperatures about 19 C. to 22.5 C.

*Time to produce a rooted young plant, summer and winter.*—About six to eight weeks at temperatures about 19 C. to 22.5 C.

*Root description.*—Medium in thickness, fibrous; typically creamy white in color, actual color of the roots is dependent on substrate composition, water quality, fertilizer type and formulation, substrate temperature and physiological age of roots.

*Rooting habit.*—Freely branching, medium density.

Plant description:

*Plant shape.*—Upright to outwardly spreading and uniform plant habit; overall shape, broadly ovate to broadly obovate.

*Growth habit.*—Freely clumping habit with about five clumps per plant imparting a bushy and dense appearance; moderately vigorous growth habit and moderate growth rate.

*Plant height, from soil level to top of leaf plane.*—About 32.9 cm.

*Plant height, from soil level to top of inflorescences.*—About 45.2 cm.

*Plant diameter or spread.*—About 56.3 cm.

Leaf description:

*Arrangement.*—Alternate; simple; about four leaves per clump.

*Length.*—About 21.7 cm.

*Width.*—About 14.2 cm.

*Shape.*—Ovate to narrowly ovate to close to narrowly deltoid.

*Apex.*—Apiculate with mucronate apex.

*Base.*—Truncate to broadly and shallowly auriculate.

*Margin.*—Entire; slightly and coarsely undulate.

*Texture and luster, upper and lower surfaces.*—Smooth, glabrous; moderately leathery; glossy.

*Venation pattern.*—Pinnate.

*Color.*—Developing leaves, upper surface: Darker than a blend of 143A and 146A. Developing leaves, lower surface: Close to a blend of 144A and 146A. Fully expanded leaves, upper surface: Slightly darker than a blend of 139A and 147A; venation, close to 143B. Fully expanded leaves, lower surface: Close to a blend of 144A and 146B; venation, close to N144C.

*Petioles.*—Length: About 21.5 cm. Diameter: Distally, about 4 mm; proximally, about 6 mm. Strength: Strong. Texture and luster, upper and lower surfaces: Smooth, glabrous; slightly glossy. Color, upper surface: Close to a blend of 143B and 144A. Color, lower surface: Close to 144A. Geniculum length: About 2.8 cm. Geniculum diameter: About 5 mm. Geniculum texture and luster, upper and lower surfaces: Smooth, glabrous; slightly glossy. Geniculum color, upper surface: Close to 144A. Geniculum color, lower surface: Close to a blend of 144A and 144B. Wing length: About 4.4 cm. Wing diameter: About 5 mm. Wing color: Close to 144A.

Inflorescence description:

*Inflorescence arrangement and flowering habit.*—Spathes with spadices held within and slightly above the foliar plane on strong and erect scapes; flowering structures arise from leaf axils; freely and continuous flowering year-round in The Netherlands; typically about twelve developing and developed inflorescences per plant at one time; inflorescence development commences about 2.5 to 3.5 months after planting.

*Inflorescence longevity.*—Spathes maintain good substance for about two months on the plant; inflorescences persistent.

*Fragrance.*—None detected.

*Spathes.*—Length: About 11.9 cm. Width: About 9 cm. Shape: Broadly ovate; strongly concave. Apex: Apiculate. Base: Shallow cordate to truncate. Margin: Entire. Texture and luster, upper and lower surfaces: Smooth, glabrous; moderately leathery; glossy. Color: When developing, front surface: Close to 45B. When developing, rear surface: Close to 46C. Fully developed, front surface: Close to a blend of 45B and 46C; with subsequent development, color becoming closer to 47B. Fully developed, rear surface: Close to 50A to 50B; with subsequent development, color becoming closer to 48A and 50B.

*Spadices.*—Length: About 4.8 cm. Diameter: About 1 cm. Shape: Columnar, tapering towards the apex; apex, obtuse; base, obtuse; in cross-section, rounded. Aspect: About 15 degrees from the peduncle axis. Color: Immature: Close to 51B; distally, close to 50A and 50B. Mature: Close to 54A and 54B. Flowers: Type: Hermaphroditic. Quantity per spadix: Numerous, about 80. Height: Less than 0.5 mm. Diameter: About 2.5 mm. Shape: Roughly square. Anther color: Close to 51B. Pollen amount: Moderate. Pollen color: Close to 155A. Stigma color: Close to 156D.

*Scape.*—Length: About 31.8 cm. Diameter: About 4 mm. Strength: Strong. Aspect: About 10 degrees from vertical. Color: Close to 144A; distally, tinged with close to 178A and 183B.

*Seed and fruit.*—To date, seed and fruit development has not been observed on plants of the new Anthurium.

Pathogen & pest resistance: To date, plants of the new Anthurium have not been observed to be resistant to pathogens or pests common to Anthurium plants.

Temperature tolerance: Plants of the new Anthurium have been observed to be tolerant to high temperatures about 30 C. and to be hardy to USDA Hardiness Zone 10.

It is claimed:

1. A new and distinct Anthurium plant named 'AN2143048' herein as illustrated and described.

* * * * *